United States Patent
Drury

(10) Patent No.: US 6,264,972 B1
(45) Date of Patent: Jul. 24, 2001

(54) TAMPON

(75) Inventor: Thomas J. Drury, Tolland, CT (US)

(73) Assignee: Tolland Development Company, LLC, Willimantic, CT (US)

( * ) Notice: Subject to any disclaimer, the term of this patent is extended or adjusted under 35 U.S.C. 154(b) by 0 days.

(21) Appl. No.: 09/437,603

(22) Filed: Nov. 10, 1999

(51) Int. Cl.⁷ ............................. A61F 13/02; A61F 6/06; A01N 25/34
(52) U.S. Cl. ...................... 424/431; 424/411; 424/430
(58) Field of Search ................................. 424/430, 431, 424/411

(56) References Cited

U.S. PATENT DOCUMENTS

| | | |
|---|---|---|
| 4,098,728 | 7/1978 | Rosenblatt . |
| 5,071,648 | 12/1991 | Rosenblatt . |
| 5,085,781 | 2/1992 | Tsuru et al. . |
| 5,370,656 | 12/1994 | Shevel . |
| 5,460,621 * | 10/1995 | Gertzman et al. .................. 604/358 |
| 5,744,150 | 4/1998 | Cerone . |
| 5,811,471 | 9/1998 | Shanbrom . |

* cited by examiner

Primary Examiner—Carlos A. Azpuru
(74) Attorney, Agent, or Firm—John S. Hale; Gipple & Hale

(57) ABSTRACT

A tampon constructed of a foamed plastic polyvinyl acetal material with an outer skin and a less dense inner central portion having a greater large pore and common pore density. The polyvinyl acetal material is impregnated with glycerine in a range of 2% to 20% concentration in a water carrier to present a soft compliant tampon.

25 Claims, 1 Drawing Sheet

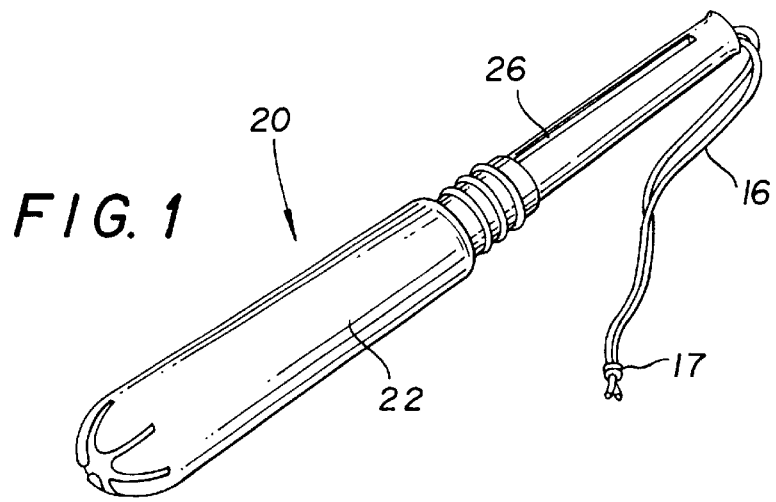
FIG. 1
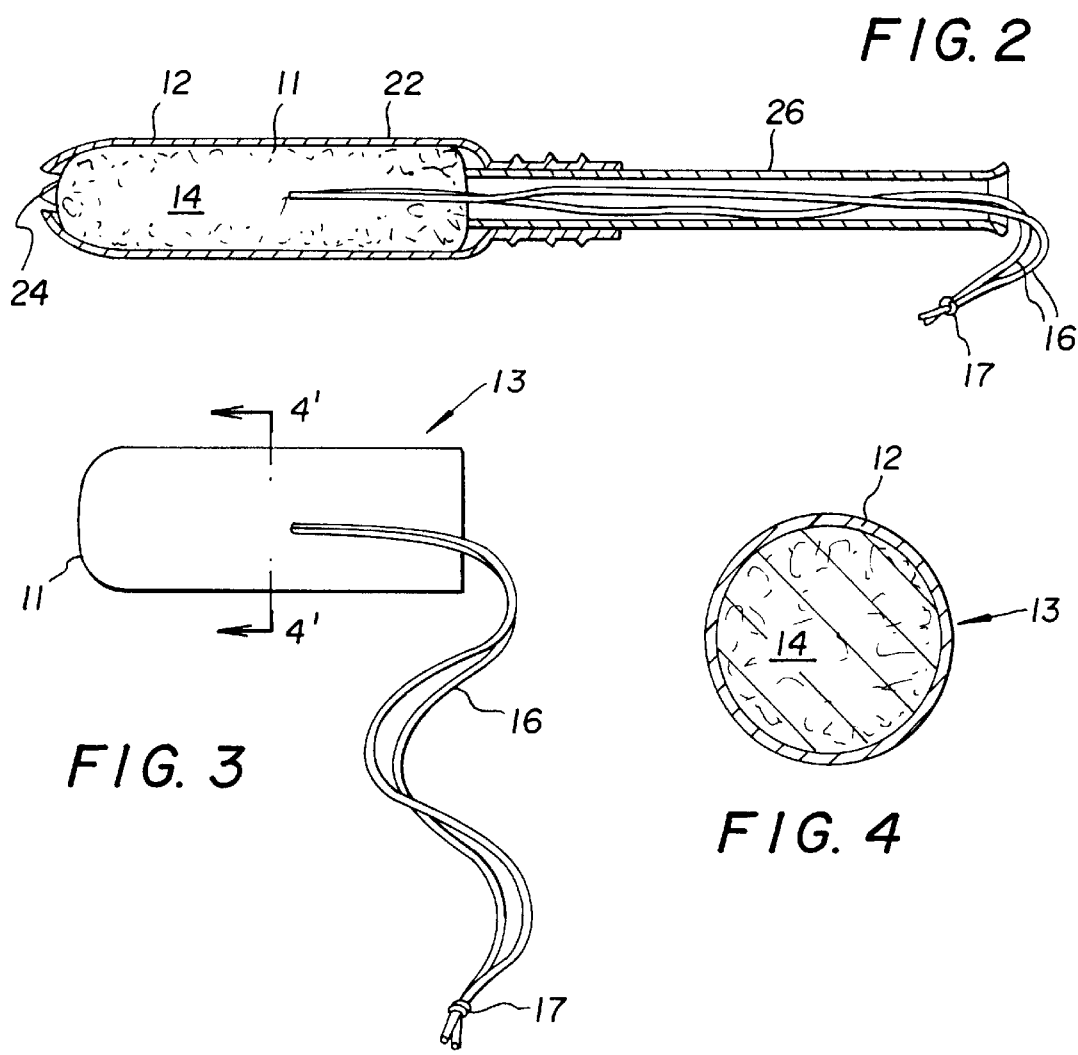
FIG. 2
FIG. 3
FIG. 4

TAMPON

FIELD OF THE INVENTION

The present invention relates generally to a tampon and more specifically relates to a tampon constructed of a novel polyvinyl acetal composition with an outer denser surface skin having an average pore size at least 25% less than the internal cross section of the tampon and the tampon body impregnated with glycerine.

BACKGROUND OF THE INVENTION

There are a number of major problems encountered in present day tampons, which are basically constructed of cellulose materials such as rayon and cotton. These tampons currently leave linting fibers and can leave fibrous fragments. Because of the cellulose composition insertion can be uncomfortable. Once a tampon is inserted there is uneven expansion, and if there is a low flow of vaginal fluids the tampon can be stiff and uncomfortable for the user. If there is a high flow of vaginal fluids the tampon can leak. In an attempt to solve the high fluid problem super absorbent tampons have been sold in the market. A problem with these absorbents are that they are large and uncomfortable. Another significant problem with the prior art tampons is that on removal the tampon can be difficult and painful to remove. Furthermore a tampon can be messy upon removal and the vaginal cavity can be left with residue which can promote harmful bacteria growth.

Rayon, a wood pulp derivative that is commonly chlorine-bleached, is more absorbent than cotton and is a commonly used material in tampons. Rayon and rayon-cotton blend fibers are widely used in the manufacture of tampons. Dioxin, found throughout the environment in varying levels, collects in the fatty tissues of animals including humans and has been found in rayon products. Considering a woman may use as many as 11,000 tampons in her lifetime, she may be subjecting herself to additional dioxin exposure.

Rayon itself may pose another risk. Results of a study recently published in *Infectious Diseases in Obstetrics and Gynecology* suggest that the use of all-cotton tampons may reduce the risk of Toxic Shock Syndrome (TSS)when compared with rayon and rayon-blend tampons. The study included 20 varieties of tampons, a polyurethane contraceptive sponge, a latex diaphragm and a polymer menstrual collection cup. All-cotton tampons did not produce the dangerous TSS toxin, *Staphylococcus aureus,* while all other varieties containing rayon amplified production of the toxin TSS-TI. While this study appears to be shaded toward cotton tampons, cotton tampons also have been shown to produce TSS and have the problems inherent with all cellulose material, namely; Tinting fibers provide a haven for bacteria as well as leaving fibrous fragments, insertion can be uncomfortable, uneven expansion, with low flow cellulose material is stiff and uncomfortable, with high flow cellulose material can leak as a portion of the packing becomes hydrated and the rest leaks down the string staining the undergarment, it can be difficult and painful to remove, can be messy upon removal, super absorbents are large and uncomfortable and cellulose material has numerous safety concerns.

The prior art discloses examples of tampons of all kinds of material and shapes to numerous to note but several examples of prior art show or indicate the use of tampons using polyvinyl acetal in their construction.

U.S. Pat. No. 4,098,728 issued Jul. 4, 1978 discloses the use of polyvinyl acetal for medical usage with a fast wicking and high liquid holding capacity.

U.S. Pat. No. 5,071,648, issued on Dec. 10, 1991 discloses a polyvinyl acetal material with a complex of iodine which forms a sponge releasing controlled amounts of iodine sufficient to kill germ cells with minimum toxicity to the surrounding tissue. The patent indicates inferentially in a list of products that polyvinyl acetal iodinized material may be utilized as a tampon.

U.S. Pat. No. 5,744,150 issued on Apr. 28, 1998 discloses a method for producing an antimicrobial iodine polyvinyl acetal sponge which is soaked in a aqueous bath of 20% to 70% triethylene glycol. The complexed sponge materials are noted as being employed in a list of goods including tampons.

U.S. Pat. No. 5,811,471, issued Sep. 22, 1998 discloses a polyvinyl acetal polymer which has a germicidal disinfectant dye bound thereto which is used as a tampon. As noted in the patent, tampons constructed of polyvinyl acetal might best use a somewhat denser, highly absorbent grade of the material. The number and size of the air bubbles in the PVA material controls these properties. Polyvinyl acetal is already used in nasal packings and other surgical packings and the same grade of PVA can be used for those applications with the invention noted in that patent.

Materials that are closely related chemically to the polyvinyl acetate-alcohol-acetal porous bodies of this invention have been used in a variety of biologically related applications. The following uses of related materials is considered exemplary and illustrative of such uses. Tan, J. H.,; et al, (Radiation Research, vol. 124, no.1, p. 43–9, October 1990) implanted a polyvinyl alcohol sponge disc in the subcutis of the thorax. A separating agent which includes a polyvinyl acetal resin having open cell structure and an average pore size of from about 10 to about 1000 micrometers has been described in U.S. Pat. No. 5,085,781 issued Feb. 4, 1992. U.S. Pat. No. 5,370,656 issued Dec. 6, 1994 describes a throat sponge which may be pre-hydrated which is made from polyvinyl acetal that is fast working and expands instantly and uniformly to absorb 23 to 27 times its weight in fluids.

The present invention solves the above noted problems with tampons in a manner not disclosed in the known prior art.

SUMMARY OF THE INVENTION

The present invention is directed toward a polyvinyl acetal tampon with a smooth outer skin having a greater density and less porosity then the foam center, ranging from 25% to 80% smaller then the internal higher porous foam center. The tampon is washed free of formaldehyde, dried and soaked in a glycerine additive in a concentration of between 2% and 20%, dried and compressed in a dry state and inserted into an applicator. The tampon is thus made soft in the dry state while still holding its compressed dimensions.

It is an object of the invention to provide a tampon which is lint free and does not fragment.

It is another object of the invention to provide a tampon which allows easy insertion and has full soft expansion.

It is yet another object of the invention to provide a tampon which becomes soft even with low vaginal flow and exhibits better fluid retention with less leakage than prior art tampons.

It is still another object of the invention to provide a tampon which allows comfortable easy removal regardless of vaginal flow level and upon removal leaves the vaginal cavity clean.

It is yet another object of the invention to provide a tampon which allows super absorbent tampons to be sized to fit a small applicator.

It is an additional object of the invention to provide a tampons which addresses TSS safety concerns and can be used with an added measure of safety.

In the accompanying drawings, there is shown an illustrative embodiment of the invention from which these and other objectives, novel features and advantages will be readily apparent.

BRIEF DESCRIPTION OF THE DRAWINGS

FIG. 1 is a perspective view of the inventive tampon in a plastic applicator;

FIG. 2 is a cross sectional view of a inventive tampon shown in FIG. 1;

FIG. 3 is a side elevation view of the tampon removed from the applicator in FIG. 1; and FIG. 4 is a cross sectional view of the inventive tampon taken along line 4'—4' of FIG. 3.

DETAILED DESCRIPTION OF THE PREFERRED EMBODIMENT

The best mode and the preferred embodimet of the novel tampon of the present invention is shown generally in FIGS. 1 through 4.

FIG. 1 illustrates an standard applicator 20 holding the tampon 11 within a chamber of the applicator for dispersion into a vaginal cavity. The tampon 11 is formed with a body 13 having an outer skin 12 and an inner more porous center 14. The outer surface is a latex like strong elastic surface for strength and durability while the inner center is a soft porous fluid absorber. A string 16 with a knotted end 17 is attached to the tampon body 13 by stitching 18 or placing the same in the cast polyvinyl acetal to allow for easy removal of the tampon from the vaginal cavity once it has been removed from the applicator and to provide longitudinal tensile strength. The string 16 can be composed of cotton, polyester, or any physiologically inert material which is soft yet sturdy enough to withstand stress after periods of immersion in a body cavity. If desired the string can be looped over the tampon body to increase tear strength. The material is then compressed from 10% to 90% depending upon the desired usage. Polyvinyl acetal has been selected of its adsorbability of fluids, ability to treated with microbial materials and because it can absorb shock through the flexible cell structure of the material while retaining rigidity allowing it to maintain shape when inserted and worn in the vaginal cavity. The applicator 20 is of standard design with a barrel 22 having an open petalled end 24 and a slidable hollow piston 26 through which the string 16 extends. The tampon retains its compressed small volume condition and is contained in the sleeve or chamber of the barrel of the applicator for insertion into a vaginal cavity. The tampon wicks up fluid from the body to expand from the initial compressed condition to a predetermined larger size to form a shaped tampon and maintain orientation. The attaching strand 16 has a length such that one end which is preferably knotted 17 is located outside of the body cavity to allow easy grasping and removal.

The base polyvinyl acetal material is heated and solublized at 190 degrees Fahrenheit, mixed with cross linking agent and catalyzed and placed into cast tubes. After removing the molded tampon material from the cast it is washed with a di-water carrier several times to remove the forming formaldehyde so that the formaldehyde is undetectable (under ½ part per million) by high pressure liquid chromatography but believed to be less than 0.1 part per million. The material is dried and then soaked for one hour in a low viscosity hydrophilic liquid lubricant such as a glycerine and is impregnated with glycerine prior to cutting and insertion into the applicator. The glycerine is preferably a 96% glycerine additive in a concentration of between 2% and 20%, preferably between 5% and 20% blended in a distilled water carrier which when soaked into the polyvinyl acetal material allows the polyvinyl acetal formulation to remain soft in dry form and hold compression. It has been found that concentrations of glycerine in excess of 20% prevent or hinder successful compression and holding of the tampon material prior to insertion into the applicator.

While glycerine is the preferred embodiment it is noted that other water soluble hygroscopic polyols could be used such ethylene glycol, propylene glycol, diethylene glycol, triethylent glycol, dipropylene glycol, tripropylene glycol, neopentyl glycol and mixtures thereof.

The cut cylinder is removed from the bath, compressed and held under compression in the applicator. The glycerine contained in the tampon acts as a slip agent to provide easy insertion of the product and a substantially friction free exit from the applicator to the user. This material is a white open-celled sponge, instantaneous fluid wicking, absorptive capacity of up to 27 times it's weight in fluids and a retained fluid capacity of up to 16 times its own weight in fluids. It is understood that the term cylindrical also includes tapered cylindrical shapes. The expanded size of the tampon is intended to approximate the size of current tampons with absorbency for each size falling within federal guidelines namely; Regular 6–9 grams, Super 9–12 grams, Super Plus 12–16 grams.

The tampon can be constructed with skin 12 having a thickness ranging from 1 micron to 100 microns and a pore size which is 25% to 80% smaller than the pore size of the center section 14. The largest pore size is reduced from 25% to 30%, preferably 27%; the average mean size is reduced from 20% to 30%, preferably 25%; and the most common pore size is reduced from 65% to 85% preferably 80%.

The preferred embodiment of the tampon is constructed with a cylindrical configuration of molded polyvinyl acetal with a skin 12 having a thickness ranging from 10 microns to 60 microns and an overall pore size which is 25% to 80% smaller than the internal center section 14. After soaking in glycerine the tampon is compressed 10% to 90%, preferably 30% and placed in a vacuum package or directly placed in an applicator 20.

The skin 12 has a smallest detected pore diameter ranging from 1.3 microns to 1.4 microns with a preferred smallest detected pore diameter of about 1.3674 microns. The smallest detected pore pressure ranges from 4.8 PSI to 4.9 PSI with a preferred smallest detected pore pressure of about 4.856 PSI. The skin has a mean flow pore diameter ranging from 22.8 microns to 23.1 microns with a preferred mean flow pore diameter of about 22.9667 microns. The skin also has a mean flow pore pressure ranging from 0.28 PSI to 0.30 PSI with a preferred mean flow pore pressure of about 0.289 PSI. The skin has a bubble point pore diameter ranging from 55.0 microns to of 62.0 microns with a preferred bubble point pore diameter of about 57.1821 microns and a bubble point pressure ranging from 0.11 PSI to 0.12 PSI with a preferred bubble point pressure of about 0.116 PSI. The skin can have a diameter at maximum pore size distribution ranging from 2.3 microns to 2.4 microns with a preferred diameter at maximum of about 2.3603 microns and a maximum pore size distribution ranging from 30.0 to 36.0 with a preferred pore size distribution of about 33.1383.

The center section 14 in the tampon has a smallest detected pore diameter ranging from 1.5 microns to 1.8 microns with a preferred smallest detected pore diameter of about 1.6759 microns with a smallest detected pore pressure ranging from 3.5 PSI to 4.2 PSI with a preferred smallest detected pore pressure of about 3.962 PSI. The center section has a mean flow pore diameter ranging from 27.5 microns to 33.5 microns with a preferred man flow pore diameter of about 30.5366 microns and a mean flow pore pressure ranging from 019 PSI to 0.23 PSI with a preferred mean flow pore pressure of about 0.217 PSI. The center section has a bubble point pore diameter ranging from 71.0 microns to 85.0 microns with a preferred bubble point pore diameter of about 78.5150 microns and a bubble point pressure ranging from 0.077 PSI to 0.93 PSI with a preferred bubble point pressure ranging from about 0.085 PSI. The center portion has a diameter at maximum pore size distribution ranging from 10.5 microns to 12.5 microns with a preferred diameter at maximum pore size distribution of about 11.5270 microns and a maximum pore size distribution ranging from 8.4 PSI to 10.2 PSI with a preferred maximum pore size distribution of about 9.3497 PSI. The method used to determine the aforenoted measurements for both the skin and center surface was a standard capillary flow analysis.

Any of a variety of substances can be introduced into the PVA after washing to remove undesired residue, e.g, by soaking or immersing the PVA in a solution of the desired substance(s) followed by drying of the PVA. This introduction occurs before soaking sponge material in the glycerine. Substances which can be readily incorporated in the PVA in this or any other suitable manner include antiviral drugs, e.g., those suitable for preventing transmission of acquired immune deficiency syndrome (AIDS); antimicrobials and/or antibiotics such as erythomycin, bacitracin, neomycin, penicilin, polymyxin B, tetracycline viomycin, chloromycetin and streptomycins, cefazolin, ampicillin, tobramycin, clindamycine and gentamycin, etc.; amino acids, peptides, vitamins, inorganic elements, co-factors for protein synthesis; hormones; synthesizers; enzymes such as collagenase, peptidases, oxidases, etc.; angiogenic drugs and polymeric carriers containing such drugs;; biocompatible surface active agents; antigenic agents. The amounts of optionally added substances can vary widely with optimum levels being readily determined in a specific case by routine experimentation. Another germicidal absorptive material for use in sanitary tampons which can be used in the present invention is disclosed in U.S. Pat. No. 5,811,471 issued Sep. 22, 1998. In this patent a polyvinyl acetal sponge is incubated in a solution of germicidal disinfectant dye which is binded to the sponge and allows the sponge to inhibit bacterial growth. It is also envisioned that the sterile albumin disclosed in U.S. Pat. No. 5,919,907 issued Jul. 6, 1999 can be used with the present invention. Another antimicrobeal treatment is disclosed in U.S. Pat. No. 5,589,072 issued Dec. 31, 1996 and can be used with the present invention.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What I claim is:

1. A tampon comprising a body made of polyvinyl acetal material with a central porous section and less porous outer skin ranging from 10 microns to about 60 microns in thickness surrounding at least a substantial portion of said central section, said outer skin having a reduction in the number of the most common pore sizes occurring the central portion of at least 70%, said material being soaked in glycerine having about 5% to about 20% concentration in a carrier to impregnate the polyvinyl acetal material with glycerine.

2. A tampon as claimed in claim 1 wherein said tampon body polyvinyl acetal material has less than ½ parts per million of formaldehyde residing in the body.

3. A tampon as claimed in claim 1 wherein said tampon body is also impregnated with antiviral drugs suitable for preventing transmission of acquired immune deficiency syndrome (AIDS).

4. A tampon as claimed in claim 1 wherein said tampon body is also impregnated with antimicrobials and/or antibiotics from the group consisting of erythomycin, bacitracin, neomycin, penicillin, polymyxin B, tetracycline, viomycin, chloromycetin and streptomycins, cefazolin, ampicillin, tobramycin, clindamycine and gentamycin.

5. A tampon as claimed in claim 1 wherein said tampon body is also impregnated from the group consisting of amino acids, peptides, vitamins, inorganic elements, co-factors for protein synthesis.

6. A tampon as claimed in claim 1 wherein said tampon body is also impregnated with antigenic agents.

7. A tampon as claimed in claim 1 wherein said tampon body is also impregnated with hormones.

8. A tampon as claimed in claim 1 wherein said tampon body is also impregnated with angiogenic drugs and polymeric carriers containing such drugs.

9. A tampon as claimed in claim 1 wherein said tampon body is also impregnated with enzymes from the group consisting of collagenase, peptidases and oxidases.

10. A tampon as claimed in claim 1 wherein said tampon includes an applicator apparatus and said polyvinyl acetal material is compressed and inserted into a chamber formed in said applicator apparatus with the walls of said chamber holding said polyvinyl acetal material under compression.

11. A tampon comprising a substantially cylindrical body made of polyvinyl acetal with a central section having a smallest detected pore pressure ranging from about 3.5 PSI to about 4.2 PSI and a smallest detected pore diameter ranging from about 1.5 microns to about 1.8 microns, and an outer skin ranging from 1 micron to about 100 microns in thickness surrounding at least the cylinder of said central section with a smallest detected pore pressure ranging from about 4.8 PSI to about 4.9 PSI and a smallest detected pore diameter ranging from about 1.3 to about 1.4 microns, said body being impregnated with glycerine in a concentration of less than 20%.

12. A tampon as claimed in claim 11 where said central section has a smallest detected pore pressure of about 4.0 PSI and said skin has a smallest detected pore pressure of about 4.9 PSI.

13. A tampon as claimed in claim 11 wherein said tampon body polyvinyl acetal material contains from 2% to 20% glycerine in the available volume of its pore spaces throughout the region of the tampon body.

14. A tampon as claimed in claim 11 wherein said polyvinyl acetal material has less than ½ part per million of formaldehyde residing in the body.

15. A tampon comprising a substantially cylindrical body made of polyvinyl acetal with a central section having a mean flow pore pressure ranging from about 0.21 PSI to about 0.22 PSI and a mean flow pore diameter ranging from about 30.0 microns to about 32.0 microns and an outer denser skin ranging from about 5 microns to about 60 microns in thickness surrounding at least the cylinder of said central section with a mean flow pore pressure ranging from about 0.28 PSI to about 0.30 PSI and a mean flow pore diameter ranging from about 21.0 microns to about 25.0 microns with a reduction of the number of the mean sized occurring pores in the central portion to the outer skin being reduced from about 20% to about 30% and said material is impregnated with a polyol selected from the group consisting of ethylene glycol, propylene glycol, diethylene glycol, triethylene glycol, dipropylene glycol, tripropylene glycol, neopentyl glycol, glycerine and mixtures thereof.

16. A tampon as claimed in claim 15 wherein said center section of polyvinyl acetal has a mean flow pore pressure of about 0.22 PSI and a mean flow pore diameter of about 30.5 microns and said skin portion has a mean pore pressure of about 0.29 PSI and a mean flow pore diameter of about 30.0 microns with a reduction of the number of the means sized occurring pores from the central portion to the outer skin being reduced about 25%.

17. A tampon as claimed in claim 15 wherein said polyol is glycerine.

18. A tampon as claimed in claim 15 wherein said polyvinyl acetal material has less than ½ parts per million of formaldehyde residing in the body.

19. A tampon comprising a substantially cylindrical body made of polyvinyl acetal with central section having an average pore size of about 23 microns and outer skin ranging from 1 micron to about 60 microns in thickness surrounding at least the cylinder of said central section with an average pore size of about 31 microns, with a reduction of the number of the largest pores from the central portion to the outer skin of about 27% and the most common pore sizes of about 80%.

20. A tampon comprising a substantially cylindrical body made of polyvinyl acetal material with a central porous section and less porous outer skin ranging from about 5 microns to about 60 microns in thickness surrounding at least a substantial portion of said central section, said outer skin having a reduction in the pore sizes occurring the central portion ranging from 25% to about 80%, said material being soaked in glycerine having about 5% to about 20% concentration in a carrier to impregnate the polyvinyl acetal material with glycerine.

21. A tampon comprising a substantially cylindrical body made of polyvinyl acetal material with a central porous section and less porous outer skin ranging from about 5 microns to about 60 microns in thickness surrounding at least a substantial portion of said central section, said outer skin having a reduction in the number of the largest pore size occurring the central portion, said material being soaked in glycerine less than 20% concentration in a carrier to impregnate the polyvinyl acetal material with glycerine, reducing the size of the substantially cylindrical body at least 10% by compressing same to form a tampon which is soft in the dry state while holding a compressed dimension.

22. A tampon as claimed in claim 21 wherein said reduction in the largest pore sizes occurring in the central portion is about 27%.

23. A tampon comprising a substantially cylindrical body made of polyvinyl acetal material with a central porous section and less porous outer skin ranging from about 5 microns to about 60 microns in thickness surrounding at least a substantial portion of said central section, said outer skin having a reduction in the number of the largest pore size occurring in the central portion, said material being soaked in glycerine of less than 20% concentration in a carrier to impregnate the polyvinyl acetal material with glycerine, compressing the polyvinyl acetal material to reduce the dimensions of same at least 10% to form a tampon which is soft in the dry state and holds a compressed dimension.

24. A tampon as claimed in claim 23 wherein said polyvinyl acetal material is compressed about 30%.

25. A tampon as claimed in claim 23 wherein said polyvinyl acetal material is compressed from 10% to 90%.

* * * * *